United States Patent [19]

Dombek

[11] Patent Number: 4,943,551

[45] Date of Patent: Jul. 24, 1990

[54] CATALYST FOR SYNTHESIS OF MIXTURES OF METHANOL AND HIGHER ALCOHOLS

[75] Inventor: Bernard D. Dombek, Charleston, W. Va.

[73] Assignee: Union Carbide Chemicals and Plastics Company, Inc., Danbury, Conn.

[21] Appl. No.: 796,411

[22] Filed: Nov. 8, 1985

[51] Int. Cl.$^5$ .................... B01J 21/06; B01J 23/04; B01J 23/12; B01J 23/72

[52] U.S. Cl. .................................. 502/345; 518/713

[58] Field of Search .................... 502/345; 518/713

[56] References Cited

U.S. PATENT DOCUMENTS

| | | | |
|---|---|---|---|
| 1,707,331 | 4/1929 | Storch | 518/713 |
| 1,741,307 | 12/1929 | Jaeger | 518/706 |
| 1,831,179 | 11/1931 | Jaeger | 518/702 |
| 2,061,470 | 11/1936 | Larson | 260/156 |
| 2,787,628 | 4/1957 | Himmler et al. | 260/449 |
| 4,181,630 | 1/1980 | Baglin et al. | 252/476 |
| 4,298,354 | 11/1981 | Hardman et al. | 44/56 |
| 4,440,668 | 4/1984 | Chang et al. | 502/331 |
| 4,451,579 | 5/1984 | Lemanski et al. | 502/306 |
| 4,477,594 | 10/1984 | Greene et al. | 518/700 |
| 4,478,955 | 10/1984 | Pesa et al. | 518/713 |
| 4,513,100 | 4/1985 | Fattore et al. | 502/303 |
| 4,522,938 | 6/1985 | Hock et al. | 502/307 |
| 4,537,909 | 8/1985 | Lin et al. | 518/713 |
| 4,567,160 | 1/1986 | Nay et al. | 502/331 X |
| 4,593,015 | 6/1986 | Hardman et al. | 502/303 |

FOREIGN PATENT DOCUMENTS

| | | |
|---|---|---|
| 0005492 | 11/1979 | European Pat. Off. |
| 608361 | 1/1935 | Fed. Rep. of Germany |
| 1159035 | 7/1969 | United Kingdom |

OTHER PUBLICATIONS

Natta et al, "Catalysis", (Emmett, P. H., Ed.), vol. V, pp. 131-174, Reinhold, N.Y., (1957).

Cohn, "Catalysis", (Emmett, P. H., Ed.), vol. IV, pp. 443-472, Reinhold, N.Y., (1956).

Storch et al., "The Fisher-Tropsch and Related Synthesis", John Wiley & Sons, Inc., N.Y., (1951), pp. 454-463.

Daly, J. Catal., vol. 89, (1984), pp. 131-137.

Maj et al., Applied Catalysis, vol. 10, (1984), pp. 313-316.

Ind. Eng. Chem. Prod. Res. Dev., vol. 20, (1981), pp. 87 to 90.

*Primary Examiner*—W. J. Shine
*Attorney, Agent, or Firm*—R. J. Finnegan

[57] ABSTRACT

Catalyst composition for the production of methanol and higher saturated aliphatic alcohols from synthesis gas. The catalysts consist essentially of:

(i) about 0.18 to about 0.81 mol fraction of copper;
(ii) about 0.045 to about 0.54 mol fraction of thorium;
(iii) up to about 0.54 mol fraction of zirconium; and
(iv) about 0.01 to about 0.2 mol fraction of an alkali metal.

7 Claims, No Drawings

4,943,551

CATALYST FOR SYNTHESIS OF MIXTURES OF METHANOL AND HIGHER ALCOHOLS

BACKGROUND OF THE INVENTION

This invention pertains to the synthesis of methanol and higher alcohols from synthesis gas and, more particularly, to the use of a catalyst consisting essentially of copper, thorium, an alkali metal, and, optionally, zirconium.

Thorium oxide has been used as a component of synthesis gas conversion catalysts for many years as shown in the text, "The Fischer-Tropsch and Related Syntheses", H. H. Storch et al., John Wiley & Sons, Inc., New York, 1951. Thorium oxide has been studied as a catalyst for the production of methanol, isobutanol, and light hydrocarbons from synthesis gas by J. J. Maj et al. in Applied Catalysis, 10. 313 (1984). Catalysts composed of copper and thorium have also been investigated as catalysts for the synthesis of methanol from hydrogen and carbon monoxide in U.S. Pat. Nos. 1,707,331, 1,741,307, 1,831,179 and 2,061,470. Several publications have described methanol production with copper-thorium catalysts, such as Ind. Eng. Chem. Prod. Res. Dev., 20. 87 (1981); J. Catal., 89. 131 (1984); and the like. In none of the above was a substantial amount of an alcohol heavier than methanol reported.

U.S. Pat. No. 4,298,354 discloses catalysts composed of copper, thorium, and alkali metal, and one or more of Ca, Mo, Rh, Mn, Pt, Ce, Cr, Zn, Al, Ti, La, V, U, Ru, Re, or Pd. The catalysts described therein are shown to produce methanol and higher alcohols. Sodium is the only alkali metal demonstrated and is described as the preferred alkali metal. All catalyst tests were carried out at 288° C, 750 psi, and with a 1:1 $H_2$/CO at a contact time of 52 seconds. This corresponds to a space velocity of 69 hr , which is an extremely low and impractical value. Productivities under such conditions are very small. With one exception, namely Example 32, which utilizes a catalyst containing rhenium, all of the catalysts described therein produced many times more isobutanol than normal butanol. Most of the examples show isobutanol as the second most abundant product after methanol. No catalysts composed only of copper, thorium, and an alkali metal promoter are disclosed, and there is no mention of zirconium as a catalyst component.

U.S. Pat. No. 4,440,668 describes a catalyst for the production of alcohols from synthesis gas which consists essentially of the oxides of copper, cobalt, zirconium, and an alkali metal. The alkali metal precipitant is preferably an alkali metal carbonate, such as sodium carbonate or potassium carbonate (column 2, lines 58+).

U.S. Pat. No. 4,451,579 is directed to a metal oxide catalyst comprising a compound selected From copper chromate, copper molybdate, and copper tungstate, a decomposable salt selected from the salts of thorium and uranium, and an alkali or alkali metal salt. These catalysts are employed in the production of low molecular weight hydrocarbons from carbon monoxide and hydrogen.

U.S. Pat. No. 4,181,630 describes the synthesis of methanol from synthesis gas using a catalyst comprising an alloy of copper and a second metal such as thorium. Examples 1 and 2 employ copper-thorium catalysts. Note, however, that the claims are directed to the catalysts and methods of preparation and are not limited to methanol synthesis.

U.S. Pat. Nos. 4,477,594, 4,478,955, 4,513,100, 4,522,938, and 4,537,909 describe copper-based catalysts employed in the conversion of synthesis gas.

The addition of methanol to gasoline as an octane improver and fuel extender is well known in the prior art. It is also well known that higher alcohols are desirable in such a fuel mixture to prevent moisture-induced phase separation of the methanol. These higher alcohols can be produced by known and established chemical processes, but it is more desirable to be able to coproduce them from synthesis gas along with the methanol.

It is an object of the instant invention to provide a process for producing methanol and higher alcohols from synthesis gas.

It is a further object of this invention to provide a mixture of methanol and higher alcohols which is suitable for direct addition to gasoline fuel compositions.

It is yet another object to provide a catalyst for converting synthesis gas to alcohol mixtures where normal butanol is Produced in amounts greater than isobutanol.

It is another object of this invention to provide catalysts for the conversion of synthesis gas to alcohol mixtures at practical space velocities and to produce an alcohol mixture containing substantial amounts of higher alcohols, even at high space velocities.

Other objects will become apparent to those skilled in the art on a further reading of the specification.

SUMMARY OF THE INVENTION

The above objects are achieved by a catalyst composition which consists essentially of:
 (i) about 0.18 to about 0.81 mol fraction of copper;
 (ii) about 0.045 to about 0.54 mol fraction of thorium;
 (iii) optionally, up to about 0.54 mol fraction of zirconium or, more narrowly, about 0.001 to about 0.54 mol fraction of zirconium; and
 (iv) about 0.01 to about 0.2 mol fraction of an alkali metal.

The invention catalyst composition, more narrowly, consists essentially of:
 (i) about 0.55 to about 0.75 mol fraction of copper;
 (ii) about 0.15 to about 0.30 mol fraction of thorium;
 (iii) about 0.02 to about 0.40 mol fraction of zirconium; and
 (iv) about 0.01 to about 0.15 mol fraction of potassium.

The form of the copper, thorium, zirconium, and alkali metal used in the catalyst of this invention is not narrowly critical. Thus they may be introduced as salts, oxides, or in free metal form, and be converted to other forms during the heating, calcining, or drying operations described later.

The catalysts of this invention are used to prepare mixtures of methanol and higher alcohols by contacting them with synthesis gas at a temperature of about 230° C. to about 320° C., a pressure of about 400 to about 2,000 psig, and a space velocity of about 500 to about 30,000 reciprocal hours ($hr^{-1}$). The preferred temperature range is about 270° C. to about 300° C. The preferred pressure range is about 800 to about 1,600 psig. The preferred space velocity is about 4,000 to about 12,000 $hr^{-1}$.

For practical purposes the catalyst composition and process variables of this invention provide a process which converts synthesis gas to a liquid product, of which at least ten percent by weight consists of alcohols higher than methanol and containing a weight ratio of normal butanol to isobutanol of at least 1:1 and with a total rate of alcohol production of at least 5 lbs./cubic foot of catalyst per hour.

The term "synthesis gas" is used herein to mean primarily a mixture of hydrogen and carbon monoxide in which the ratio of hydrogen:carbon monoxide is about 0.1:1 to about 6:1 and preferably 0.2:1 to 4:1. Synthesis gas can be obtained by heating coke in the presence of air and then steam. It can also produced by the partial oxidation of coal, natural gas, or petroleum hydrocarbons such as methane. The synthesis gas also known as "water gas" usually contains small amounts of impurities such as carbon dioxide, nitrogen, and the like. If desired, mixtures of carbon monoxide and hydrogen can be also used.

The method of carrying out the process of this invention is not narrowly critical and can be carried out in a continuous or batch operation with a fixed bed heterogeneous catalyst or a fluidized bed catalyst.

The reactor used is also not narrowly critical and thus any apparatus known to those skilled in this art can be used.

The invention is further described in the examples which follow. All parts and percentages are by weight unless otherwise specified.

DESCRIPTION OF THE INVENTION

1. A catalyst of the following composition was prepared where the subscripts represent parts of the respective metals on a molar basis: $Cu_{0.63}$, $Th_{0.18}$, $Zr_{0.09}$, and $K_{0.09}$.

A solution of 15.46 g $Cu(NO_3)_2 \cdot 3H_2O$ and 9.94 g Th$(NO_3)_4 \cdot 4H_2O$ was prepared by dissolving the sa in 100 ml of $H_2O$. Powdered ZrO (1.11 g) was suspended in this solution, and it was heated to 60° C. A solution of 15.0 g of $Na_2CO_3$ at 60° C. was added rapidly to this solution with agitation. The mixture was stirred for four hours while cooling to room temperature, and the precipitate was collected on a filter and washed well with distilled water. The solid was dried at 100° C. and calcined in air at 100° C. for two hours. It was then impregnated with a solution of 0.98 g of potassium acetate in water and dried at 50° C. The material was again calcined at 400° C. for two hours and was pressed into pellets. After crushing the pellets, particles in the 30/40 mesh range (1.2 g) were loaded into a catalyst tube constructed of 316 stainless steel. The catalyst was reduced under 1 atmosphere of 2% $H_2/N_2$ at a space velocity of 1,300 hr$^{-1}$ beginning at a temperature of 100° C. The temperature was raised at a rate of 2° C./minute until 250° C. was attained, where it was held for about fifteen hours. A mixture of 0.5:1 $H_2/CO$ was then passed over the catalyst at a pressure of 900 psi and a space velocity of 9,000 hr$^{-1}$, and the temperature was raised to 285° C. Under these conditions, the catalyst produced a mixture consisting mainly of methanol and higher alcohols. The catalyst exhibited a carbon efficiency to alcohols of 94% and a rate to alcohols of 24 lbs/cubic foot of catalyst per hour. The liquid product analysis is given below:

| | |
|---|---|
| Methanol | 78% |
| Ethanol | 11.6% |
| i-Propanol | 0.6% |
| n-Propanol | 3.9% |
| i-Butanol | 0.4% |
| n-Butanol | 3.2% |

Approximately 1.5% of ester products was also observed, consisting mainly of methyl acetate and methyl propionate.

This is a very typical product distribution for the Cu, Th, and Zr containing catalysts whose test results are shown below. In the remaining examples, products identified $C_2+$ as are oxygenates of molecular weight hig than methanol, and a distribution similar to the above-is observed.

In the examples given below, C eff is the percent carbon efficiency to alcohols, defined as the percent fraction of the total CO converted to organic products which is converted to alcohols; $C_2+$ is the fraction of the alcohol product which is not methanol; and the rate is given in pounds of alcohol product/cubic foot of catalyst per hour. Unless specified otherwise in all of the following examples, the pressure is 900 psi, the temperature is 285? C., the space velocity is 9,000 hr$^{-1}$, and the $H_2/CO$ ratio is 0.5.

A catalyst prepared as in Example 1 was operated under a variety of conditions, as documented in Tables 1-4 below. Under all of these conditions, the catalyst produces more normal butanol than isobutanol.

TABLE 1

Reaction at Different Temperatures

| T, °C. | C eff | $C_2+$ | Rate |
|---|---|---|---|
| 230 | 99 | 17 | 8 |
| 250 | 99 | 18 | 13 |
| 285 | 98 | 23 | 20 |
| 300 | 96 | 24 | 20 |
| 320 | 95 | 29 | 18 |

TABLE 2

Reaction at Different Pressures

| P, psi | C eff | $C_2+$ | Rate |
|---|---|---|---|
| 400 | 99 | 27 | 8 |
| 900 | 98 | 23 | 20 |

TABLE 3

Reaction at Different Space Velocities

| GHSV | C eff | $C_2+$ | Rate |
|---|---|---|---|
| 510 | 72 | 23 | 0.9 |
| 4000 | 95 | 23 | 10 |
| 9000 | 98 | 23 | 20 |
| 20000 | 99 | 22 | 36 |

TABLE 4

Reaction with Different Gas Compositions

| $H_2/CO/CO_2$ | C eff | $C_2+$ | Rate |
|---|---|---|---|
| 17/83/0 | 99 | 29 | 19 |
| 33/67/0 | 99 | 23 | 20 |
| 50/50/0 | 99 | 16 | 22 |
| 67/33/0* | 99 | 12 | 21 |
| 70/20/10 | 99 | 28 | 2 |

*Liquid analysis of the Product formed under these conditions:

| | |
|---|---|
| Methanol | 87% |
| Ethanol | 8% |
| i-Propanol | 0.3% |
| n-Propanol | 1.2% |
| i-Butanol | 0.17% |
| n-Butanol | 1.7% |

TABLE 5

Examples with Copper-Thorium Catalysts

| Ex. | | | | C eff | $C_2+$ | Rate |
|---|---|---|---|---|---|---|
| 2(comp) | Cu 0.500 | Th 0.500 | | 82 | 7 | 26 |
| 3 | Cu 0.400 | Th 0.500 | K 0.100 | 90 | 12 | 22 |
| 4 | Cu 0.190 | Th 0.780 | K 0.029 | 90 | 8 | 33 |
| 5 | Cu 0.600 | Th 0.300 | K 0.100 | 93 | 16 | 28 |
| 6 | Cu 0.700 | Th 0.200 | K 0.100 | 95 | 20 | 22 |
| 7 | Cu 0.630 | Th 0.250 | K 0.120 | 96 | 16 | 20 |

Table 5 illustrates that inclusion of potassium in copper-thorium catalysts improves the effectiveness of these catalysts for alcohol production, and specifically improves the efficiency to alcohols and the yield of $C_2+$ alcohols Example 2 is a comparative example showing that the absence of an alkali metal results in a relatively poor catalyst.

TABLE 6

Examples Showing Relatively Poor Performance of Catalysts Containing Certain Other Metals in Place of Zirconium

| Ex. | | | C eff | $C_2+$ | Rate |
|---|---|---|---|---|---|
| 8(comp) | Cu 0.500 Th 0.200 | Zn 0.200 K 0.100 | 70 | 4 | 6 |
| 9(comp) | Cu 0.500 Th 0.200 | Cr 0.200 K 0.100 | 76 | 5 | 7 |
| 10(comp) | Cu 0.300 Th 0.200 | Mn 0.400 K 0.100 | 80 | 9 | 6 |
| 11 | Cu 0.500 Th 0.200 | Zr 0.200 K 0.100 | 91 | 25 | 20 |

TABLE 7

Examples Showing Relatively Poor Performance of Catalysts Containing Certain Other Metals in Place of Thorium
(Conditions: 300° C., $H_2/CO = 2$, GHSV = 4000)

| Ex. | | | C eff | $C_2+$ | Rate |
|---|---|---|---|---|---|
| 12(comp) | Cu 0.450 | Cr 0.180 Zr 0.270 K 0.090 | 95 | 1.5 | 14 |
| 13(comp) | Cu 0.300 | Cr 0.300 Zr 0.300 K 0.100 | 95 | 2.5 | 14 |
| 14(comp) | Cu 0.200 | Ti 0.500 Zr 0.200 K 0.100 | 92 | 7.0 | 2.3 |
| 15(comp) | Cu 0.640 | Al 0.180 Zr 0.090 K 0.090 | 95 | 7.0 | 13 |
| 16 | Cu 0.640 | Th 0.180 Zr 0.090 K 0.090 | 95 | 10 | 13 |

TABLE 8

Further Examples Showing That Replacement of Thorium By Other Metals Does Not Yield Good Catalysts

| Ex. | | C eff | $C_2+$ | Rate |
|---|---|---|---|---|
| 17*(comp) | Cu 0.630 Ce 0.180 Zr 0.090 K 0.100 | 94 | 10 | 15 |
| 18*(comp) | Cu 0.630 Hf 0.180 Zr 0.090 K 0.100 | 100 | 8 | 10 |
| 19*(comp) | Cu 0.560 Ce 0.180 Zr 0.180 K 0.080 | 98 | 8 | 12 |
| 20*(comp) | Cu 0.500 Ce 0.200 Zr 0.200 K 0.100 | 90 | 11 | 9 |

*Control or comparative examples

TABLE 9

Catalysts With Varying Compositions of Copper, Thorium, and Zirconium

| Ex. | | C eff | $C_2+$ | Rate |
|---|---|---|---|---|
| 21 | Cu 0.640 Th 0.180 Zr 0.090 K 0.090 | 98 | 22 | 23 |
| 22 | Cu 0.810 Th 0.045 Zr 0.045 K 0.100 | 80 | 18 | 13 |
| 23 | Cu 0.430 Th 0.430 Zr 0.045 K 0.100 | 98 | 13 | 17 |
| 24 | Cu 0.045 Th 0.810 Zr 0.045 K 0.100 | 100 | 0 | .03 |
| 25 | Cu 0.045 Th 0.430 Zr 0.430 K 0.100 | 100 | 15 | 6 |
| 26 | Cu 0.045 Th 0.045 Zr 0.810 K 0.100 | 60 | 19 | 3 |
| 27 | Cu 0.430 Th 0.045 Zr 0.430 K 0.100 | 100 | 12 | 14 |
| 28 | Cu 0.180 Th 0.540 Zr 0.180 K 0.100 | 99 | 19 | 13 |
| 29 | Cu 0.180 Th 0.180 Zr 0.540 K 0.100 | 100 | 13 | 12 |
| 30 | Cu 0.300 Th 0.300 Zr 0.300 K 0.100 | 90 | 17 | 15 |

TABLE 9-continued

Catalysts With Varying Compositions of Copper, Thorium, and Zirconium

| Ex. | | C eff | $C_2+$ | Rate |
|---|---|---|---|---|
| 31 | Cu 0.720 Th 0.090 Zr 0.090 K 0.100 | 99 | 15 | 19 |
| 32 | Cu 0.590 Th 0.270 Zr 0.045 K 0.100 | 99 | 19 | 18 |
| 33 | Cu 0.590 Th 0.045 Zr 0.270 K 0.100 | 100 | 13 | 18 |
| 34 | Cu 0.200 Th 0.400 Zr 0.300 K 0.100 | 80 | 22 | 13 |
| 35 | Cu 0.300 Th 0.200 Zr 0.400 K 0.100 | 92 | 15 | 20 |

TABLE 10

Copper/Thorium/Zirconium Catalysts With Several Alkali and Alkaline Earth Metals

| Ex. | | | | | C eff | $C_2+$ | Rate |
|---|---|---|---|---|---|---|---|
| 36 | Cu 0.640 | Th 0.180 | Zr 0.090 | K 0.090 | 98 | 22 | 23 |
| 37 | Cu 0.630 | Th 0.180 | Zr 0.090 | Na 0.100 | 92 | 11 | 21 |
| 38 | Cu 0.630 | Th 0.180 | Zr 0.090 | Li 0.100 | 94 | 8 | 19 |
| 39 | Cu 0.630 | Th 0.180 | Zr 0.090 | Cs 0.100 | 99 | 11 | 16 |
| 40 | Cu 0.630 | Th 0.180 | Zr 0.090 | Mg 0.100 | 90 | 9 | 16 |
| 41 | Cu 0.630 | Th 0.180 | Zr 0.090 | Ca 0.100 | 96 | 7 | 15 |
| 42 | Cu 0.630 | Th 0.180 | Zr 0.090 | Ba 0.100 | 97 | 6 | 20 |
| 43 | Cu 0.670 | Th 0.190 | Zr 0.090 | Ba 0.050 | 98 | 9 | 20 |

Although the invention has been described with a certain amount of particularity, it will be realized by those skilled in the art that certain changes and modifications can be made without departing from the spirit and scope of the claimed invention.

I claim:

1. Catalyst composition for the production of methanol and higher saturated aliphatic alcohols from synthesis gas consisting essentially of:
   (i) about 0.18 to about 0.81 mol fraction of copper;
   (ii) about 0.045 to about 0.54 mol fraction of thorium;
   (iii) up to about 0.54 mol fraction of zirconium; and
   (iv) about 0.01 to about 0.2 mol fraction of an alkali metal.

2. Composition of claim 1 wherein the alkali metal is potassium.

3. Catalyst composition for the production of methanol and higher saturated aliphatic alcohols from synthesis gas consisting essentially of:
   (i) about 0.55 to about 0.75 mol fraction of copper;
   (ii) about 0.15 to about 0.30 mol fraction of thorium;
   (iii) about 0.02 to about 0.40 mol fraction of zirconium; and
   (iv) about 0.0I to about 0.15 mol fraction of potassium.

4. Catalyst composition for the production of methanol and higher saturated aliphatic alcohols from synthesis gas consisting essentially of:
   (i) about 0.18 to about 0.81 mol fraction of copper;
   (ii) about 0.045 to about 0.54 mol fraction of thorium;
   (iii) about 0.001 to about 0.54 mol fraction of zirconium; and
   (iv) about 0.01 to about 0.2 mol fraction of an alkali metal.

5. Composition of claim 4 wherein the alkali metal is potassium.

6. Catalyst composition for the production of methanol and higher saturated aliphatic alcohols from synthesis gas consisting of:
   (i) about 0.18 to about 0.81 mol fraction of copper;
   (ii) about 0.045 to about 0.54 mol fraction of thorium; and
   (iii) about 0.01 to about 0.2 mol fraction of an alkali metal.

7. Composition of claim 6 wherein the alkali metal is potassium.

* * * * *